(12) United States Patent
Tsai et al.

(10) Patent No.: US 11,986,680 B2
(45) Date of Patent: *May 21, 2024

(54) NEUTRON CAPTURE THERAPY SYSTEM COMPRISING A BEAM SHAPING ASSEMBLY CONFIGURED TO SHAPE A NEUTRON BEAM (71) Applicant: NEUBORON MEDTECH LTD., Jiangsu (CN)

(72) Inventors: Chiung-Wen Tsai, Jiangsu (CN); Weilin Chen, Jiangsu (CN); Ming-Chen Hsiao, Jiangsu (CN); Yuanhao Liu, Jiangsu (CN)

(73) Assignee: NEUBORON MEDTECH LTD., Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/892,254

(22) Filed: Aug. 22, 2022

(65) Prior Publication Data

US 2022/0409932 A1 Dec. 29, 2022

Related U.S. Application Data (63) Continuation of application No. 16/798,644, filed on Feb. 24, 2020, now Pat. No. 11,458,336, which is a (Continued)

(30) Foreign Application Priority Data

Aug. 24, 2017 (CN) .......................... 201710733144.1
Aug. 24, 2017 (CN) .......................... 201721063911.4

(51) Int. Cl.
*A61N 5/10* (2006.01)
*G21G 4/00* (2006.01)
(Continued)

(52) U.S. Cl.
CPC ............. *A61N 5/1077* (2013.01); *A61N 5/10* (2013.01); *A61N 5/1048* (2013.01);
(Continued)

(58) Field of Classification Search
CPC ...... A61N 5/10; A61N 5/1077; A61N 5/1078; A61N 2005/1087; A61N 2005/1089;
(Continued)

(56) References Cited

U.S. PATENT DOCUMENTS 5,870,447 A * 2/1999 Powell ...................... G21G 1/10
376/190
7,005,623 B2 * 2/2006 Neuberger ............ G01J 1/0425
250/559.1
(Continued)

FOREIGN PATENT DOCUMENTS

CN 105120952 A 12/2015
CN 106552321 A 4/2017
(Continued)

*Primary Examiner* — Allen C. Ho
(74) *Attorney, Agent, or Firm* — Locke Lord LLP; Tim Tingkang Xia, Esq.

(57) ABSTRACT

The present disclosure provides a neutron capture therapy system, including an accelerator for generating a charged particle beam, a neutron generator for generating a neutron beam having neutrons after irradiation by the charged particle beam, and a beam shaping assembly for shaping the neutron beam. The beam shaping assembly includes a moderator and a reflecting assembly surrounding the moderator. The neutron generator generates the neutrons after irradiation by the charged particle beam. The moderator moderates the neutrons generated by the neutron generator to a preset energy spectrum. The reflecting assembly includes a reflecting assembly to deflected neutrons back to the neutron beam and a supporting member to support the reflectors. A lead-antimony alloy is for the reflecting assembly to mitigate a
(Continued)

creep effect that occurs when only a lead material is for the reflectors, thereby improving the structural strength of a beam shaping assembly.

20 Claims, 4 Drawing Sheets

Related U.S. Application Data continuation of application No. PCT/CN2018/100572, filed on Aug. 15, 2018.

(51) Int. Cl.
G21G 4/02 (2006.01)
G21K 1/02 (2006.01)

(52) U.S. Cl.
CPC .......... *A61N 5/1064* (2013.01); *A61N 5/1065* (2013.01); *A61N 5/1067* (2013.01); *A61N 5/1071* (2013.01); *A61N 5/1078* (2013.01); *G21G 4/00* (2013.01); *G21G 4/02* (2013.01); *G21K 1/02* (2013.01); *G21K 1/025* (2013.01); *A61N 2005/1012* (2013.01); *A61N 2005/1085* (2013.01); *A61N 2005/109* (2013.01); *A61N 2005/1094* (2013.01)

(58) Field of Classification Search
CPC ...... A61N 2005/109; G21G 4/00; G21G 4/02; G21K 1/02; G21K 1/025
USPC .................. 378/64, 65, 147–149; 250/493.1
See application file for complete search history.

(56) References Cited

U.S. PATENT DOCUMENTS

| | | | | |
|---|---|---|---|---|
| 7,263,170 B2 * | 8/2007 | Pellegrino | ................ | G21K 1/10 378/115 |
| 9,743,912 B2 * | 8/2017 | Fichtinger | ............ | A61N 5/1027 |
| 9,889,320 B2 * | 2/2018 | Liu | .......................... | G21K 1/10 |
| 9,974,979 B2 * | 5/2018 | Liu | ...................... | A61N 5/1077 |
| 10,157,693 B2 * | 12/2018 | Liu | .......................... | A61N 5/10 |
| 10,328,286 B2 * | 6/2019 | Liu | ..................... | C04B 35/6455 |
| 10,434,333 B2 * | 10/2019 | Liu | ..................... | A61N 5/1077 |
| 10,462,893 B2 * | 10/2019 | Park, Jr. | .................. | G21G 4/02 |
| 10,537,750 B2 * | 1/2020 | Liu | ...................... | A61N 5/1049 |
| 10,556,127 B2 * | 2/2020 | Liu | ...................... | A61N 5/1082 |
| 10,639,499 B2 * | 5/2020 | Liu | .......................... | H05H 6/00 |
| 10,744,345 B2 * | 8/2020 | Liu | ...................... | A61N 5/1042 |
| 10,773,104 B2 * | 9/2020 | Liu | .......................... | H05H 6/00 |
| 10,791,618 B2 * | 9/2020 | Hsueh Liu | ............... | H05H 3/06 |
| 10,898,731 B2 * | 1/2021 | Liu | ...................... | A61N 5/1077 |
| 10,898,733 B2 * | 1/2021 | Liu | ...................... | A61N 5/1081 |
| 10,926,108 B2 * | 2/2021 | Liu | .......................... | G21K 1/10 |
| 10,926,110 B2 * | 2/2021 | Liu | ...................... | A61N 5/1049 |
| 10,994,154 B2 * | 5/2021 | Liu | ......................... | B33Y 80/00 |
| 11,024,437 B2 * | 6/2021 | Park, Jr. | .................. | G21G 1/10 |
| 11,058,898 B2 * | 7/2021 | Liu | ...................... | A61N 5/1064 |
| 11,198,023 B2 * | 12/2021 | Chen | ........................ | G21K 5/04 |
| 11,224,766 B2 * | 1/2022 | Liu | .......................... | G21K 5/04 |
| 11,266,859 B2 * | 3/2022 | Liu | .......................... | H05H 3/06 |
| 11,338,155 B2 * | 5/2022 | Hsiao | ...................... | H05H 3/06 |
| 11,400,314 B2 * | 8/2022 | Hsiao | .................. | A61B 6/4258 |
| 11,400,316 B2 * | 8/2022 | Liu | .......................... | C04B 41/83 |
| 11,458,336 B2 * | 10/2022 | Tsai | ...................... | A61N 5/1067 |
| 11,559,705 B2 * | 1/2023 | Chen | ................ | A61K 41/0095 |
| 11,561,308 B2 * | 1/2023 | Liu | .......................... | G01T 1/02 |
| 11,740,370 B2 * | 8/2023 | Liu | .......................... | H05H 3/06 250/391 |
| 11,813,483 B2 * | 11/2023 | Liu | .......................... | A61N 5/10 |
| 2004/0227056 A1 | 11/2004 | Neuberger et al. | | |
| 2007/0076851 A1 | 4/2007 | Pellegrino | | |
| 2012/0330084 A1 | 12/2012 | Pantell et al. | | |
| 2014/0121501 A1 | 5/2014 | Fichtinger et al. | | |
| 2018/0169440 A1 | 6/2018 | Liu et al. | | |
| 2018/0250528 A1 | 9/2018 | Liu et al. | | |
| 2018/0326225 A1 | 11/2018 | Liu et al. | | |
| 2019/0262632 A1 | 8/2019 | Liu et al. | | |

FOREIGN PATENT DOCUMENTS

| | | |
|---|---|---|
| CN | 106552322 A | 4/2017 |
| CN | 106975162 A | 7/2017 |
| CN | 206835439 U | 1/2018 |
| EP | 3032926 A1 | 6/2016 |
| EP | 2979728 B1 | 2/2018 |
| JP | 1962010400 | 8/1962 |
| JP | 2007242422 A | 9/2007 |
| JP | 2008022920 A | 2/2008 |
| JP | 2013024566 A | 2/2013 |
| JP | 2018112761 A | 7/2018 |
| RU | 2013147424 A | 4/2015 |
| WO | 2017080344 A1 | 5/2017 |

* cited by examiner

NEUTRON CAPTURE THERAPY SYSTEM COMPRISING A BEAM SHAPING ASSEMBLY CONFIGURED TO SHAPE A NEUTRON BEAM

CROSS-REFERENCE TO RELATED PATENT APPLICATION

This application is a continuation of U.S. patent application Ser. No. 16/798,644, filed on Feb. 24, 2020 and issued as U.S. Pat. No. 11,458,336 B2 on Oct. 4, 2022, which is a continuation application of International Application No. PCT/CN2018/100572, filed on Aug. 15, 2018, which claims priority to Chinese Patent Application No. 201710733144.1, filed on Aug. 24, 2017; Chinese Patent Application No. 201721063911.4, filed on Aug. 24, 2017, the disclosures of which are hereby incorporated by reference.

FIELD

The present disclosure relates generally to a radiotherapy system, and, more particularly to a neutron capture therapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radio resistant malignant tumors (such as glioblastomamultiforme and melanoma).

For the purpose of reducing radiation damage to the normal tissue surrounding a tumor site, target therapy in chemotherapy has been employed in the radiotherapy. While for high-radio resistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

Figure 1:
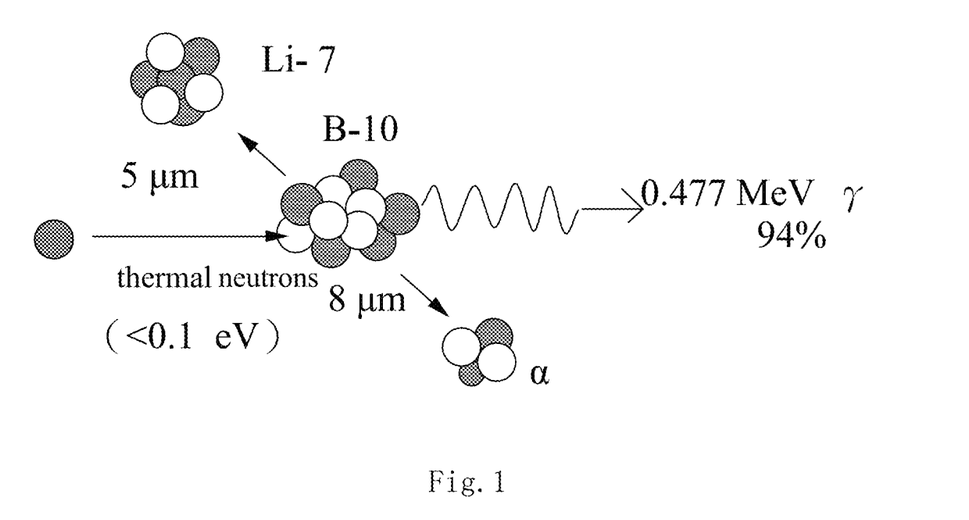
FIG. 1 is a schematic view of the boron neutron capture reactions according to the present disclosure.

BNCT takes advantage that the boron ($^{10}B$)-containing pharmaceuticals have high neutron capture cross section and produces $^4He$ and $^7Li$ heavy charged particles through $^{10}B(n,\alpha)^7Li$ neutron capture and nuclear fission reaction. As illustrated in FIG. 1, a schematic view of boron neutron capture reaction are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7Li$ are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

In accelerator-based BNCT, in one aspect, neutrons or other particles such as y rays generated by a neutron generator are radioactive, and in another aspect, neutrons generated by the neutron generator generally need to undergo a beam shaping assembly to adjust an energy spectrum and increase neutron yield. Therefore, a reflecting assembly needs to be installed to reduce a particle leakage rate, adjust an energy spectrum, and increase neutron yield. Lead is a conventional material used for reflection or shielding. However, lead has a significant creep effect and cannot provide structural rigidity and a long service life. For BNCT, neutron beam quality depends on the beam shaping assembly and also depends on the reflecting assembly and a shielding assembly. Lead is usually used as a reflection material in the prior art. However, the creep effect of lead results in insufficient structural precision, and as a result the safety of the entire BNCT is affected.

Therefore, it is really necessary to provide a new technical solution so as to solve the foregoing problem.

The statements in this section merely provide background information related to the present disclosure and may not constitute prior art.

SUMMARY

To resolve the foregoing technical problem, an aspect of the present invention provides a neutron capture therapy system, so that the structural strength/precision of a beam shaping assembly can be increased without significantly affecting neutron beam quality. The neutron capture therapy system includes an accelerator configured to generate a charged particle beam; a neutron generator configured to generate a neutron beam having neutrons after irradiation by the charged particle beam; a beam shaping assembly configured to shape the neutron beam, wherein the beam shaping assembly includes a moderator configured to moderate the neutrons generated by the neutron generator to a preset energy spectrum and a reflecting assembly surrounding the moderator; wherein the reflecting assembly includes a plurality of reflectors configured to guide deflected neutrons back to the neutron beam to increase intensity of the neutrons in the preset energy spectrum and a supporting member configured to hold the reflectors.

Further, the reflecting assembly includes a plurality of cells correspondingly forming a plurality of cores, each of the cells forms one of the cores, each of the cores has an accommodating space, the cores are connected to form the supporting member, and the reflectors are correspondingly disposed in the accommodating spaces of the cores.

Further, the supporting member is integrally formed, and the reflectors are formed by pouring a material of the reflectors into the accommodating spaces of the cores.

More particularly, a specified quantity of cores are connected to form the supporting member, the reflecting assembly further includes a top plate, a bottom plate disposed opposite to the top plate and side plates connecting to the top plate and the bottom plate and surrounding the cores, the specified quantity of cores, the reflector disposed in the accommodating spaces of the cores, the top plate, the bottom plate and the side plates correspondingly form a plurality of reflecting modules, and the reflecting modules are stacked to form the reflecting assembly surrounding the moderator.

Further, at least one of materials of the cores, the top plate, the bottom plate and the side plates is made of a material with a low neutron absorption cross section and low activity with neutrons, and a proportion of a total volume of the material of the core, the top plate, the bottom plate and the side plates in a volume of the material of the reflectors is less than 10%.

Further, the material of the reflectors is lead, and at least one of the materials of the cores, the top plate, the bottom plate and the side plates is lead-antimony alloy.

Further, equivalent total antimony content in the lead-antimony alloy material is less than 1%.

To resolve the foregoing technical problem, another aspect of the present invention provides a neutron capture therapy system, so that the structural strength/precision of a beam shaping assembly can be increased without significantly affecting neutron beam quality. The neutron capture therapy device includes a beam shaping assembly configured to shape a neutron beam having neutrons, wherein the beam shaping assembly includes a moderator configured to moderate the neutrons to a preset energy spectrum, a reflecting assembly surrounding the moderator, and a shielding assembly surrounding the reflecting assembly; wherein the shielding assembly includes a supporting member configured to hold the reflecting assembly and a plurality of shieldings arranged in the supporting member.

Further, the shielding assembly includes a plurality of cells correspondingly forming a plurality of cores, each of the cells forms one of the cores, each of the cores has an accommodating space, the shieldings are correspondingly disposed in the accommodating spaces of the cores, and the cores are connected to form the supporting member.

More particularly, a cross section of each of the cores is a hexagon.

Further, the supporting member is integrally formed, and the shieldings are formed by pouring a material of the shieldings into the accommodating spaces of the cores.

Further, a specified quantity of cores are connected to form the supporting member, a top plate, a bottom plate disposed opposite to the top plate and side plates that connect the top plate and the bottom plate and surround the cores are provided outside the supporting member, the specified quantity of connected cores, the shielding disposed in the cores, the top plate, the bottom plate, and the side plates correspondingly form a plurality of shielding modules, and the shielding modules are stacked to form the shielding assembly.

Particularly, a material of the shieldings is lead, a material of the core, the top plate, the bottom plate and the side plates is a material with a low neutron absorption cross section and low activity with neutrons.

Further, a proportion of a total volume of the material of the core, the top plate, the bottom plate, and the side plates in a volume of the material of the shieldings is less than 10%.

Particularly, the reflecting assembly includes a plurality of reflectors configured to guide deflected neutrons back to the neutron beam to increase intensity of neutrons in the preset energy spectrum and the supporting member configured to support the reflector, a material of the reflectors is lead, and a material of the supporting member is aluminum alloy or lead-antimony alloy.

To resolve the foregoing technical problem, another aspect of the present invention provides a neutron capture therapy system, so that the structural strength/precision of a beam shaping assembly can be increased without significantly affecting neutron beam quality. The neutron capture therapy device includes a beam shaping assembly configured to shape a neutron beam having neutrons, wherein the beam shaping assembly includes a moderator configured to moderate the neutrons to a preset energy spectrum and a reflecting assembly surrounding the moderator; wherein the reflecting assembly includes a plurality of reflectors configured to guide deflected neutrons back to the neutron beam to increase intensity of the neutrons in the preset energy spectrum and a plurality of cells for supporting the reflectors, the cells correspondingly form a plurality of cores, each of the cells forms one of the cores, each of the cores has an accommodating space configured to receive one of the reflectors or a material configured to shield the neutrons.

Further, the cores are connected to form a supporting member, a top plate and a bottom plate disposed opposite to the top plate and side plates that connect the top plate and the bottom plate and surround the cores are provided outside the supporting member.

Further, a material of the core, the top plate, the bottom plate, and the side plates is a material with a low neutron absorption cross section and low activity with neutrons, and a proportion of a total volume of the material of the core, the top plate, the bottom plate, and the side plates in a volume of a material of the reflectors is less than 10%.

Particularly, the cores are connected to form a supporting member, the supporting member is integrally formed, and the material is poured into the accommodating space.

Further, the cores are connected to form a supporting member, the material in the accommodating space is lead, and a material of the supporting member is aluminum alloy or lead-antimony alloy.

Compared to the prior art, by means of the neutron capture therapy system in the present application, the supporting member of the reflector or/and the supporting member of the shielding assembly are disposed to support a reflection material or/and a shielding material, and alloy material with a low neutron absorption and low activity is to support lead to overcome the creep effect of the lead material, so that the structural strength of a beam shaping assembly is increased without affecting neutron beam quality.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

The embodiments of the present disclosure are further described in detail below with reference to the accompanying drawings, so that those skilled in the art can implement the technical solutions according to the description.

The following description of the preferred embodiments is merely exemplary in nature and is in no way intended to limit the invention, its application, or uses.

A reflecting assembly needs to be installed to reduce a particle radiation leakage rate and a shielding assembly needs to be installed to provide safe shielding against radiation for particles (for example, neutrons) generated by an accelerator. Lead or a lead alloy is a conventional material for reflection or shielding. However, lead has a significant creep effect and cannot provide structural rigidity and a long service life.

Figure 2:
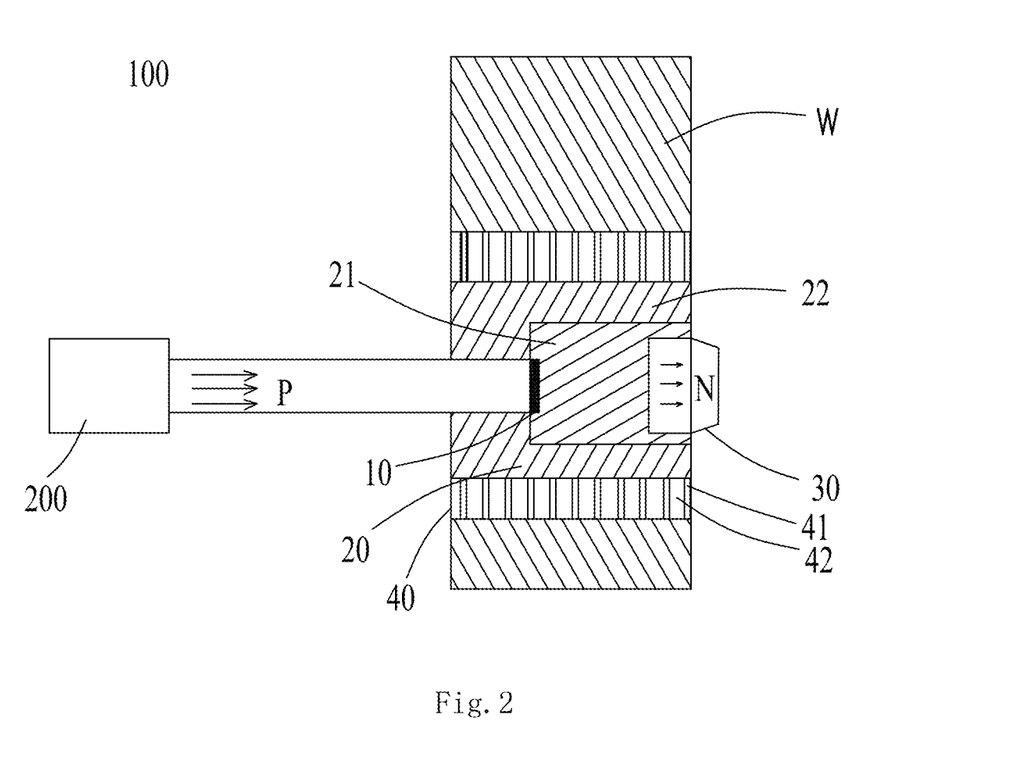
FIG. 2 is a schematic view of a neutron capture therapy system installed in a shielding wall according to a first embodiment of the present disclosure, wherein the neutron capture therapy system has a shielding assembly, and only the shielding assembly has a supporting member.
Figure 3:
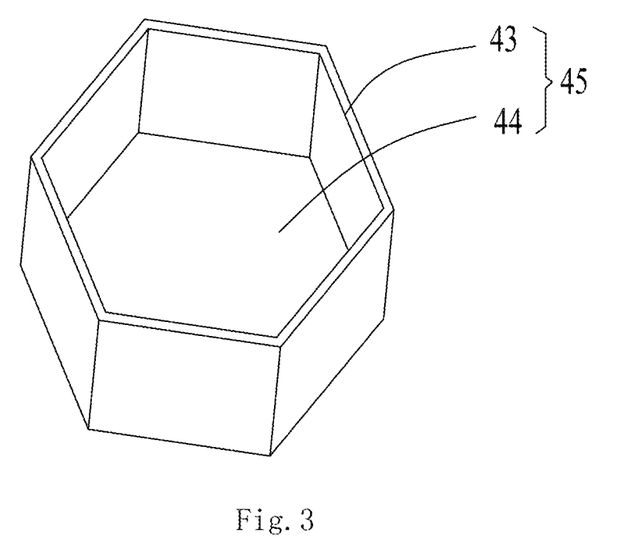
FIG. 3 is a schematic view of a core structure of the shielding assembly according to the first Embodiment of the present disclosure.

As shown in FIG. 2, the present disclosure provides a neutron capture therapy system 100. The neutron capture therapy system 100 includes an accelerator 200 for generating a charged particle beam P, a neutron generator 10 for generating a neutron beam N after irradiation by the charged particle beam P, a beam shaping assembly 20 for shaping a neutron beam N, and a collimator 30. The beam shaping assembly 20 includes a moderator 21 and a reflecting assembly 22 surrounding the moderator 21. The neutron generator 10 is configured to generate the neutron beam N after being irradiated by a charged particle beam P. The moderator 21 moderates the neutron beam N generated by the neutron generator 10 to a preset energy spectrum. The reflecting assembly 22 guides deflected neutrons back to the neutron beam N to increase the intensity of neutrons in the preset energy spectrum. The collimator 30 concentrates neutrons generated by the neutron generator 10.

In a first embodiment, the neutron capture therapy system 100 further includes a shielding assembly 40. Referring to FIG. 2, the shielding assembly 40 includes a supporting member 41 and a plurality of shieldings 42 disposed in the supporting member 41. The supporting member 41 includes a plurality of cells 43 correspondingly forming a plurality of cores 45, each cell 43 forms a core 45 having an accommodating space 44, the shieldings 42 are correspondingly disposed in the accommodating spaces 44, and the cores 45 are connected to form the supporting member 41. In a preferred embodiment, the supporting member 41 is integrally formed, and the shieldings 42 are formed by pouring the material of the shieldings 42 into the accommodating space 44 of each core 45 of the supporting member 41.

Figure 4:
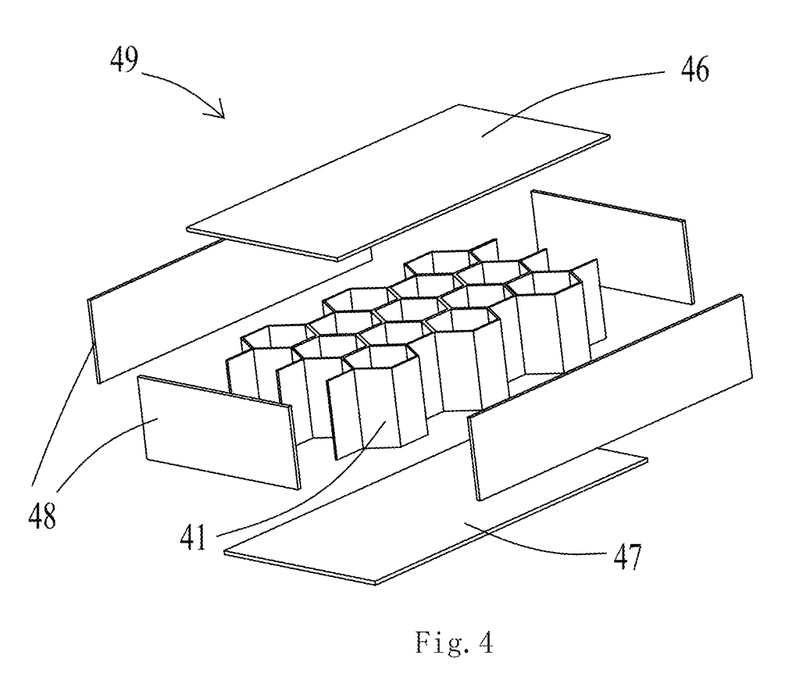
FIG. 4 is a schematic exploded view of a shielding module without a shielding according to the first embodiment of the present disclosure.

Referring to FIG. 4, a specified quantity of cores 45 are connected to form the supporting member 41, and the supporting member 41 has a hexagonal cross section and facilitates formation and stacking. A top plate 46, a bottom plate 47 disposed opposite to the top plate 46 and four side plates 48 that connect the top plate 46 and the bottom plate 47 and surround the cores 45 are provided outside the supporting member 41. The specified quantity of connected cores 45, the shielding 42 disposed in the core 45, the top plate 46, the bottom plate 47, and the side plates 48 form a shielding module 49, and shielding modules 49 are stacked to form the shielding assembly 40. In the present disclosure, to facilitate subsequent stacking of the shielding modules 49, in a preferred embodiment, the specified quantity is 20. Certainly, a person skilled in the art may adjust the quantity of the side plates 48 according to a design requirement, for example, to 3 or 6. A specified quantity of the shielding modules 49 is adjusted according to a design requirement, for example, to 10 or 30.

The material of the shielding assembly 40 is lead, and the top plate 46, the bottom plate 47, and the side plates 48 are made of an alloy material with a low neutron absorption cross section and low neutron activity. To minimize the impact of an alloy material on neutron beam quality, the proportion of the total volume of the alloy material in the volume of the material of the shielding assembly 40 is less than 10%.

In this embodiment, the reflecting assembly 22 is a structure that is made of lead and has a creep effect. The shielding assembly 40 is surrounding the reflecting assembly 22. The beam shaping assembly 20 is embedded in a shielding wall W to shield against radioactive rays generated in an irradiation room. The shielding assembly 40 is directly supported in the shielding wall W. The supporting member 41 inside the shielding assembly 40 supports the shielding 42 and at the same time reinforces the strength of the reflecting assembly 22, so that the structural strength of the entire beam shaping assembly 20 is increased.

Figure 5:
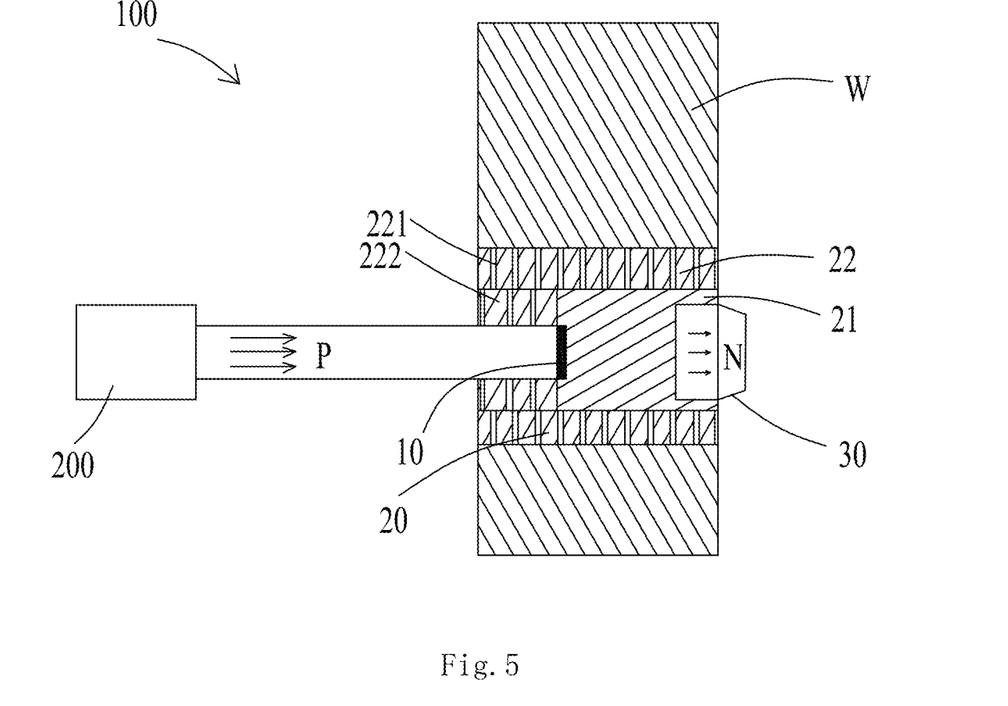
FIG. 5 is a schematic view of a neutron capture therapy system installed in a shielding wall according to a second embodiment of the present disclosure, wherein the beam shaping assembly does not have a shielding assembly, and only a reflecting assembly has a supporting member.
Figure 6:
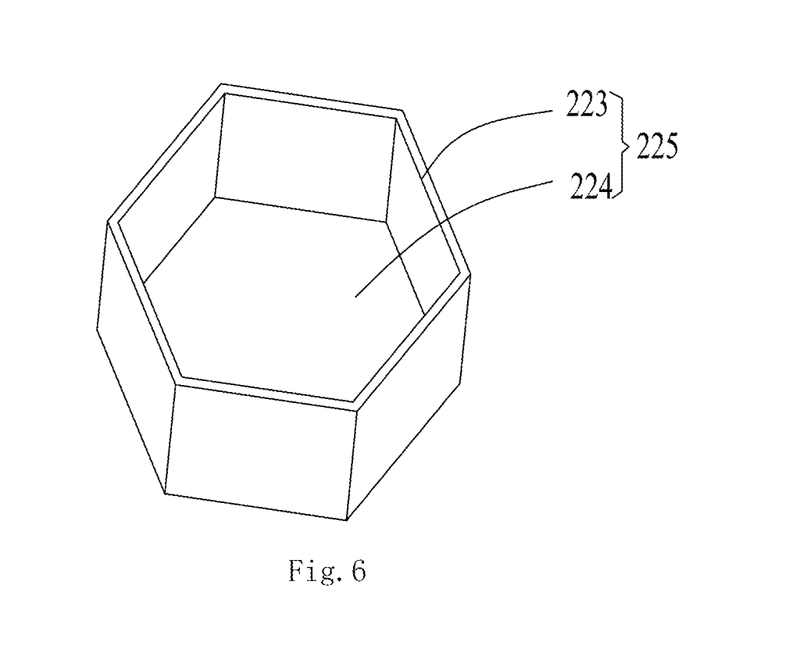
FIG. 6 is a schematic view of a core structure of the reflecting assembly according to the second embodiment of the present disclosure.

As shown in FIG. 5, in a second embodiment, the arrangement of the shielding assembly 40 in the first embodiment is directly applied to the reflecting assembly 22, the reflecting assembly 22 is disposed to be a structure that includes a supporting member 221 without the shielding assembly 40.

Referring to FIG. 5, the reflecting assembly 22 includes a supporting member 221 and a plurality of reflectors 222 disposed in the supporting member 221. The supporting member 221 includes a plurality of cells 223 correspondingly forming a plurality of cores 225, and each cell 223 forms a core 225 having an accommodating space 224. The reflectors 222 are correspondingly disposed in the accommodating spaces 224 of the cores 225, and the cores 225 are connected to form the supporting member 221. In a preferred embodiment, the supporting member 221 is integrally, and the reflectors 222 are formed by pouring the material of the reflectors 222 into the cores 225 of the supporting member 221.

Figure 7:
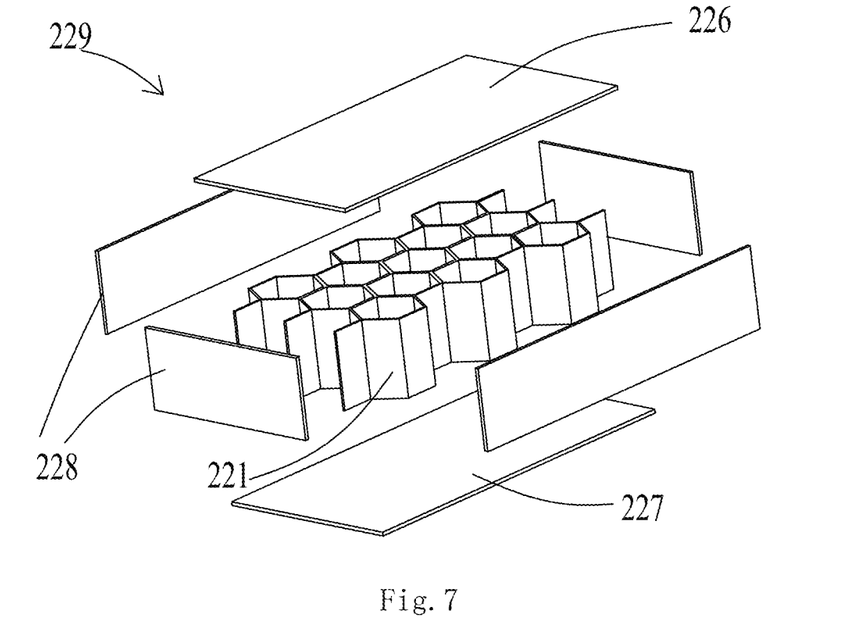
FIG. 7 is a schematic exploded view of a reflecting module without a reflector according to second embodiment of the present disclosure.

As shown in FIG. 7, a modular design is applied for the reflecting assembly 22. Specifically, a specified quantity of cores 225 are connected to form the supporting member 221, a top plate 226, a bottom plate 227 disposed opposite to the top plate and four side plates 228 that connect the top plate 226 and the bottom plate 227 and surround the cores 225 are provided outside the supporting member 221. The specified quantity of connected cores 225, the reflector 222 disposed in the core 225, the top plate 226, the bottom plate 227, and the side plates 228 form a reflecting module 229, and reflecting modules 229 are stacked to form the reflecting assembly 22. The top plate 226, the bottom plate 227, and the four side plates 228 that are connected to the top plate 226 and the bottom plate 227 and surrounding the cores 225 are made of an alloy material with a low neutron absorption cross section and low activity, and the proportion of the total volume of the alloy material in the volume of the material of the shielding assembly 42 is less than 10%.

Figure 8:
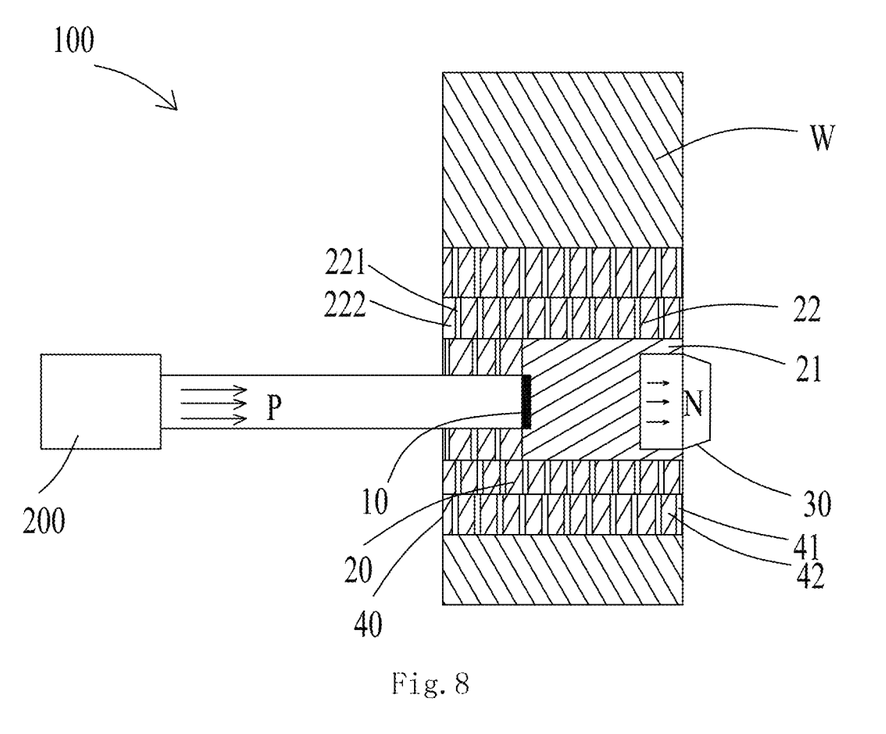
FIG. 8 is a schematic view of a neutron capture therapy system installed in a shielding wall according to a third embodiment of the present disclosure, wherein both the reflector and the shielding portion have supporting members.

FIG. 8 shows a third embodiment of the present disclosure. The third embodiment is different from the foregoing embodiments in that the structural design with a supporting member is configured to both the reflecting assembly and the shielding assembly. In this embodiment, the reflectors are disposed in the same manner in which the reflectors are disposed in the second embodiment, the shielding assembly is disposed in the same manner in which the shielding assembly is disposed in the first embodiment, and details are therefore not described herein again. When the beam shaping assembly 20 is embedded in the shielding wall W, the shielding assembly 40 is directly supported in the shielding wall W. In this embodiment, the supporting member 221 is disposed to support the reflectors 222 and the supporting member 41 is disposed to support the shieldings 42 without affecting neutron beam quality, to overcome the structural precision problem caused by a creep effect that occurs in the used lead material of the reflecting assembly and the shielding assembly.

It should be pointed out that as discussed in the second embodiment and third embodiment, when the reflecting assembly is disposed to be a structure that has a reflecting module, the reflecting assembly 22 is surrounding the moderator 21, and an outer surface of the moderator 21 is generally cylindrical or has at least one conical structure. Therefore, when the reflecting assembly formed by stacking the reflecting modules 229 is surrounding the moderator 21, the structural combination should further be considered. The structure of the reflecting module that is directly combined with the surface of the moderator 21 is adjusted. For example, the reflecting module that is in contact with the moderator 21 is cut to attach the reflecting assembly to the outer surface of the moderator 21, so that the reflection of deflected neutrons by the reflector 222 in the reflecting assembly 22 is not affected.

Each of the cores formed by the cells in the present disclosure may be any closed structure having a hole-shaped accommodating space, for example, a geometrical structure whose cross section is a square, a triangle or a hexagon, a tetrahedron, and an octahedron or a dodecahedron having a hole-shaped accommodating space, or configured to be alternatively a non-closed structure having a hole-shaped accommodating space. Examples are not enumerated herein. The lead is disposed in the hole-shaped accommodating space through pouring to be closely surrounded by the material of the cores, so that the alloy material of the cores supports the lead material.

In the second embodiment and the third embodiment of the present disclosure, to facilitate stacking and manufacturing of the reflecting module and/or the shielding module, a structure whose cross section is a hexagon is configured for both the cores of the reflecting assembly and the cores of the shielding assembly. Certainly, the structure of the supporting member of the reflecting assembly may be alternatively different from the structure of the supporting member of the shielding assembly. For example, the structure of the supporting member of the cores of the shielding assembly is a geometrical shape whose cross section is a hexagon, and the structure of the supporting member of the cores of the reflecting assembly is a tetrahedron, provided that an alloy material of the supporting member can support the lead material and has low impact on neutron beam quality. Details are not described herein again.

In all the foregoing embodiments, in consideration of the weight of the entire beam shaping assembly, an alloy material with light weight is applied for the cores, the top plate, the bottom plate, and the side plates that connect the top plate and the bottom plate and surround the cores, in consideration of neutron beam quality, a material with low neutron absorption cross section and low activity should further be chosen for the material of the core, the top plate, the bottom plate, and the side plates, and the proportion of the total volume of the material of the top plate, the bottom plate, the side plates, and the core in the volume of the material of the reflector or the material of the shielding is less than 10%. In the present disclosure, aluminum alloy material is preferentially chosen for the material of the top plate, the bottom plate, the side plates, and the core. Lead-antimony alloy may be alternatively applied in place of the aluminum alloy for the following reason. The neutron absorption cross section of lead-antimony alloy material is higher than that of an aluminum alloy material. However, the proportion of the total volume of the material of the top plate, the bottom plate, the side plates, and the core in the volume of the material of the reflector or the material of the shielding assembly is less than 10%, the equivalent total antimony content is less than 1%. Therefore, antimony in lead-antimony alloy material does not have significant impact on neutron beam quality.

The reflectors or/and the shieldings in the beam shaping assembly of the present disclosure are made of lead having a creep effect. However, when the beam shaping assembly is embedded in the shielding wall W of the irradiation room, the supporting member made of the alloy may provide supporting to the reflectors or/and the shieldings made of the lead material with the creep effect supported in the shielding wall W. Therefore, the structural precision of the entire beam shaping assembly is increased.

For the shielding assembly in the present disclosure, in one aspect, alloy is disposed to support lead, and in another aspect, the top plate, the bottom plate, and the side plates that connect the top plate and the bottom plate are disposed surrounding the lead supported by the alloy. In this way, the modular design of the shielding assembly is implemented while the structural strength of the shielding assembly is reinforced, and the structure is simple. Therefore, the shielding assembly in the present disclosure may be alternatively applied to other shielding scenarios.

The beam shaping assembly for neutron capture therapy disclosed in the present disclosure is not limited to the content in the foregoing embodiments and the structures represented in the accompanying drawings. All obvious changes, replacements or modifications made to the materials, shapes, and positions of the members based on the present disclosure fall within the protection scope of the present disclosure.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A beam shaping assembly configured to shape a neutron beam having neutrons, comprising:
   a moderator configured to moderate the neutron beam to a preset energy spectrum; and
   a reflecting assembly surrounding the moderator;
   wherein the reflecting assembly comprises:
      a plurality of reflectors configured to guide deflected neutrons back to the neutron beam to increase an intensity of the neutron beam in the preset energy spectrum; and
      a supporting member configured to hold the plurality of reflectors.

2. The beam shaping assembly according to claim 1, wherein the reflecting assembly further comprises a plurality of cells correspondingly forming a plurality of cores, each of the plurality of cells forms one of the plurality of cores, the plurality of cores have a plurality of accommodating spaces, each of the plurality of cores has a corresponding accommodating space of the plurality of accommodating spaces, the plurality of reflectors are correspondingly disposed in the plurality of accommodating spaces of the plurality of cores, and the plurality of cores are connected to form the supporting member.

3. The beam shaping assembly according to claim 2, wherein the supporting member is integrally formed, and the plurality of reflectors comprise a material disposed in the plurality of accommodating spaces of the plurality of cores.

4. The beam shaping assembly according to claim 2, wherein the reflecting assembly further includes a top plate, a bottom plate disposed opposite to the top plate, and side plates connecting to the top plate and the bottom plate and surrounding the plurality of cores, wherein the plurality of cores, the plurality of reflectors disposed in the plurality of accommodating spaces of the plurality of cores, the top plate, the bottom plate, and the side plates correspondingly form a reflecting module.

5. The beam shaping assembly according to claim 4, wherein the plurality of cores, the top plate, the bottom plate, and the side plates comprise a material with a low neutron absorption cross section and a low activity with neutrons, and a proportion of a total volume of the plurality of cores, the top plate, the bottom plate, and the side plates in a volume of the plurality of reflectors is less than 10%.

6. The beam shaping assembly according to claim 5, wherein the plurality of reflectors comprise lead, and the plurality of cores, the top plate, the bottom plate, and the side plates comprise lead-antimony alloy.

7. The beam shaping assembly according to claim 6, wherein an equivalent total antimony content in the lead-antimony alloy is less than 1%.

8. A beam shaping assembly configured to shape a neutron beam having neutrons, comprising:
   a moderator configured to moderate the neutron beam to a preset energy spectrum;
   a reflecting assembly surrounding the moderator; and
   a shielding assembly surrounding the reflecting assembly;
   wherein the shielding assembly comprises:
      a supporting member configured to hold the reflecting assembly; and
      a plurality of shieldings arranged in the supporting member.

9. The beam shaping assembly according to claim 8, wherein the shielding assembly further comprises a plurality of cells correspondingly forming a plurality of cores, each of the plurality of cells forms one of the plurality of cores, the plurality of cores have a plurality of accommodating spaces, each of the plurality of cores has a corresponding accommodating space of the plurality of accommodating spaces, the plurality of shieldings are correspondingly disposed in the plurality of accommodating spaces of the plurality of cores, and the plurality of cores are connected to form the supporting member.

10. The beam shaping assembly according to claim 9, wherein a cross section of each of the plurality of cores is a hexagon.

11. The beam shaping assembly according to claim 9, wherein the supporting member is integrally formed, and the plurality of shieldings comprise a material disposed in the plurality of accommodating spaces of the plurality of cores.

12. The beam shaping assembly according to claim 9, wherein the reflecting assembly further includes a top plate, a bottom plate disposed opposite to the top plate, and side plates connecting to the top plate and the bottom plate and surrounding the plurality of cores provided outside the supporting member, wherein the plurality of cores, the plurality of shieldings disposed in the plurality of cores, the top plate, the bottom plate, and the side plates correspondingly form a shielding module.

13. The beam shaping assembly according to claim 9, wherein the plurality of shieldings comprise lead, and wherein the plurality of cores, the top plate, the bottom plate, and the side plates comprise a material with a low neutron absorption cross section and a low activity with neutrons.

14. The beam shaping assembly according to claim 13, wherein a proportion of a total volume of the plurality of cores, the top plate, the bottom plate, and the side plates in a volume of the plurality of shieldings is less than 10%.

15. The beam shaping assembly according to claim 8, wherein the reflecting assembly comprises a plurality of reflectors configured to guide deflected neutrons back to the neutron beam to increase an intensity of the neutron beam in the preset energy spectrum, and the supporting member configured to support the plurality of reflectors, the plurality of reflectors comprise lead, and the supporting member comprises aluminum alloy or lead-antimony alloy.

16. A beam shaping assembly configured to shape a neutron beam having neutrons, comprising:
   a moderator configured to moderate the neutron beam to a preset energy spectrum; and
   a reflecting assembly surrounding the moderator;
   wherein the reflecting assembly comprises:
      a plurality of reflectors configured to guide deflected neutrons back to the neutron beam to increase an intensity of the neutron beam in the preset energy spectrum; and
      a plurality of cells configured to support the plurality of reflectors, the plurality of cells correspondingly forms a plurality of cores, each of the plurality of cells forms one of the plurality of cores, each of the plurality of cores has an accommodating space, the accommodating space is configured to receive one of the plurality of reflectors or to receive a material configured to form a shielding, and the shielding is configured to shield the neutrons.

17. The beam shaping assembly according to claim 16, wherein the plurality of cores are connected to form a supporting member, the reflecting assembly further includes a top plate, a bottom plate disposed opposite to the top plate, and side plates connecting to the top plate and the bottom plate and surrounding the plurality of cores provided outside the supporting member.

18. The beam shaping assembly according to claim 17, wherein the plurality of cores, the top plate, the bottom plate, and the side plates comprises a material with a low neutron absorption cross section and a low activity with neutrons, and a proportion of a total volume of the plurality of cores, the top plate, the bottom plate, and the side plates in a volume of the plurality of reflectors is less than 10%.

19. The beam shaping assembly according to claim 16, wherein the plurality of cores are connected to form a supporting member, the supporting member is integrally formed, and the shielding comprises the material deposited in the accommodating space.

20. The beam shaping assembly according to claim 16, wherein the plurality of cores are connected to form a supporting member, the material in the accommodating space comprises lead, and the supporting member comprises aluminum alloy or lead-antimony alloy.

* * * * *